United States Patent [19]
Kinkead et al.

[11] Patent Number: 5,626,820
[45] Date of Patent: May 6, 1997

[54] CLEAN ROOM AIR FILTERING

[76] Inventors: Devon A. Kinkead, 10 Hector Ave., Cumberland, R.I. 02864; Robert W. Rezuke, 127 Worcester Rd., North Grafton, Mass. 01536; John K. Higley, 14 Saddlebrook Rd., Sherborn, Mass. 01770

[21] Appl. No.: 161,931

[22] Filed: Dec. 2, 1993

Related U.S. Application Data

[63] Continuation-in-part of Ser. No. 807,151, Dec. 13, 1991, abandoned, which is a continuation-in-part of Ser. No. 283,318, Dec. 12, 1988, abandoned.

[51] Int. Cl.$^6$ .......................... A62B 7/08; B05B 15/12; B01D 46/00
[52] U.S. Cl. .......................... 422/122; 454/53; 454/187; 95/285; 95/287; 55/279; 55/318; 55/327; 55/385.2; 55/485
[58] Field of Search .......................... 422/122; 427/180, 427/185, 244, 346, 366, 557, 559; 454/187, 53; 55/279, 318, 327, 332, 385.2, 485; 95/285, 287

[56] References Cited

U.S. PATENT DOCUMENTS

| | | | |
|---|---|---|---|
| 1,585,113 | 5/1926 | Robert | 96/136 |
| 3,015,367 | 1/1962 | Smith et al. | 96/135 |
| 3,170,808 | 2/1965 | Almy et al. | 427/559 |
| 3,196,871 | 7/1965 | Hormats et al. | 128/205.28 |
| 3,220,915 | 11/1965 | Shannon | 428/194 |
| 3,226,251 | 12/1965 | Norton et al. | 427/244 |
| 3,294,572 | 12/1966 | Piccione et al. | 117/47 |
| 3,375,933 | 4/1968 | Rodman | 210/502.1 |
| 3,381,454 | 5/1968 | Sponsel | 502/159 |
| 3,525,378 | 8/1970 | Root | 427/244 |
| 3,690,852 | 9/1972 | Smith et al. | 427/201 |
| 3,697,347 | 10/1972 | Lehmann | 156/181 |
| 3,764,561 | 10/1973 | Nishino et al. | 252/447 |
| 3,779,244 | 12/1973 | Weeks, Jr. et al. | 128/146.2 |
| 3,800,516 | 4/1974 | Paluch | 55/354 |
| 3,870,495 | 3/1975 | Dixson et al. | 55/489 |
| 3,912,567 | 10/1975 | Schwartz | 156/167 |
| 3,925,021 | 12/1975 | Yoshino et al. | 96/118 |
| 3,956,458 | 5/1976 | Anderson | 423/210 |
| 3,995,005 | 11/1976 | Teller | 423/210 |

(List continued on next page.)

FOREIGN PATENT DOCUMENTS

| | | |
|---|---|---|
| 4221592A1 | 1/1994 | Germany . |
| 0034475 | 3/1979 | Japan . |
| 0262537 | 11/1986 | Japan . |
| 2-126912 | 5/1990 | Japan . |
| 433186 | 9/1935 | United Kingdom . |
| 2013102A | 8/1978 | United Kingdom . |
| 2077141A | 12/1981 | United Kingdom . |
| WO90/05549 | 5/1990 | WIPO . |

OTHER PUBLICATIONS

Muller et al., "Measurement of Airborne Concentrations and Surface Arrival Rates of Organic Contaminants in Clean Rooms," viewgraphs from 1993 IES Meeting, Las Vegas, NV (MAy 2–7, 1993).

(List continued on next page.)

Primary Examiner—Nina Bhat
Attorney, Agent, or Firm—Fish & Richardson P.C.

[57] ABSTRACT

The invention features a clean room and a chemical air filter suitable for use in the air handling system of the clean room directly upstream of high-efficiency particulate air (HEPA) filters. The chemical filter is of the pleated filter type comprising an air permeable, relatively thick web of non-woven fibrous carrier material of pleated form. The web includes a matrix formed of a large multiplicity of synthetic fibers and is characterized in that activated carbon particles are distributed throughout the web, bound in the interstices of the matrix in a manner preventing loss to the air of particles in quantity substantially detrimental to the performance of the HEPA filter. The activated carbon particles are of the type selected to remove the predetermined gas-phase contaminant from the air from the source. The invention also features a non-off gassing filter casing that may easily be installed into existing clean room air handling systems.

19 Claims, 8 Drawing Sheets

U.S. PATENT DOCUMENTS

| | | | |
|---|---|---|---|
| 3,998,988 | 12/1976 | Shimomai et al. | 428/400 |
| 4,007,301 | 2/1977 | De Martino | 427/244 |
| 4,011,067 | 3/1977 | Carey, Jr. | 55/354 |
| 4,072,479 | 2/1978 | Sinha et al. | 55/73 |
| 4,075,282 | 2/1978 | Storp et al. | 423/230 |
| 4,081,501 | 3/1978 | Muther | 264/518 |
| 4,132,650 | 1/1979 | Kirsch et al. | 210/491 |
| 4,160,059 | 7/1979 | Samejima | 428/288 |
| 4,171,410 | 10/1979 | Frob | 521/52 |
| 4,188,960 | 2/1980 | Morie et al. | 131/345 |
| 4,201,838 | 5/1980 | Goldberg | 429/145 |
| 4,215,682 | 8/1980 | Kubik et al. | 128/205.29 |
| 4,225,642 | 9/1980 | Hirakawa | 428/91 |
| 4,277,266 | 7/1981 | Dick | 55/381 |
| 4,285,748 | 8/1981 | Booker et al. | 156/167 |
| 4,315,965 | 2/1982 | Mason et al. | 428/198 |
| 4,344,775 | 8/1982 | Klein | 95/137 |
| 4,376,675 | 3/1983 | Perrotta | 162/145 |
| 4,379,802 | 4/1983 | Weaver et al. | 428/220 |
| 4,530,272 | 7/1985 | Stokes | 454/187 |
| 4,578,256 | 3/1986 | Nishino et al. | 423/210 |
| 4,595,575 | 6/1986 | Oeste et al. | 423/210 |
| 4,643,182 | 2/1987 | Klein | 128/201.25 |
| 4,660,464 | 4/1987 | Tanaka | 98/115.3 |
| 4,664,683 | 5/1987 | Degen et al. | 502/402 |
| 4,680,040 | 7/1987 | Gooray et al. | 96/152 |
| 4,693,173 | 9/1987 | Saiki et al. | 454/187 |
| 4,696,837 | 9/1987 | Lindner | 427/255.3 |
| 4,699,681 | 10/1987 | Kasmark, Jr. et al. | 55/316 |
| 4,704,972 | 11/1987 | Marchand | 110/345 |
| 4,724,874 | 2/1988 | Parikh et al. | 141/98 |
| 4,737,173 | 4/1988 | Kudirka et al. | 55/276 |
| 4,749,390 | 6/1988 | Burnett et al. | 55/316 |
| 4,772,455 | 9/1988 | Izumi et al. | 423/210 |
| 4,792,491 | 12/1988 | Atkinson et al. | 428/408 |
| 4,793,837 | 12/1988 | Pontius | 502/62 |
| 4,873,914 | 10/1989 | Hirayama | 454/187 |
| 4,963,069 | 10/1990 | Wurst et al. | 414/416 |
| 4,983,192 | 1/1991 | von Blucher et al. | 55/387 |
| 4,985,280 | 1/1991 | Scholz et al. | 427/244 |
| 5,030,423 | 7/1991 | Obee et al. | 422/122 |
| 5,037,624 | 8/1991 | Tom et al. | 423/210 |
| 5,042,997 | 8/1991 | Rhodes | 55/126 |
| 5,053,064 | 10/1991 | Hama et al. | 55/270 |
| 5,064,626 | 11/1991 | Johnson et al. | 423/245 |
| 5,096,477 | 3/1992 | Shinoda et al. | 454/187 X |
| 5,122,170 | 6/1992 | Satoh et al. | 55/316 |
| 5,143,752 | 9/1992 | Nakajima et al. | 427/244 |
| 5,165,595 | 11/1992 | Horio et al. | 236/49.3 |
| 5,166,530 | 11/1992 | McCleary | 250/492.2 |
| 5,181,819 | 1/1993 | Sakata et al. | 454/187 X |
| 5,213,767 | 5/1993 | Smith et al. | 422/177 |
| 5,221,573 | 6/1993 | Baigas, Jr. | 428/281 |
| 5,271,780 | 12/1993 | Baigas, Jr. | 156/62.6 |
| 5,271,997 | 12/1993 | Baigas, Jr. | 428/233 |
| 5,344,626 | 9/1994 | Abler | 423/210 |
| 5,413,527 | 5/1995 | Dansui et al. | 454/57 |

OTHER PUBLICATIONS

Brochure, "Vaporsorb Effects on Wafer Surface Properties," Published by Extraction Systems Inc. (Sep. 1992).

"Dual Function Air Filter," Press Release, ASHRAE Journal, Nov. 1989.

"Air Processing System", Chilton's IAN, Dec. 1989.

"HEPA Filter System," Medical Product Manufacturing News, Nov. 1989.

"Air Processing System," Biomedical Products, Jul. 1989.

Kelly et al., "Testing of chemically treated adsorbent air purifiers", ASHRAE Journal, pp. 14–23, Jul. 1993.

Advertisement, EACI Enviroco, "Check Our Room–Side Manner", Dec. 1992.

Devon A. Kinkead, "Pleated DPCC–based adsorbers: New technology for air purification", ASHRAE Journal, pp. 35–40, Nov. 1990.

Slade et al., "Utilization of Established Air Pollution Monitoring Networks in Ontario Following Nuclear Incidents", Atomic Energy of Canada Limited, Apr. 1988.

Devon A. Kinkead, "The Incorporation and Use of Reagent Impregnated Activated Carbons in Nonwoven Webs", American Filtration Society, Mar. 1988.

Kinkead et al., "Semiconductor Process Stabilization Using Gas Phase Filtration (Part I)".

Extraction Systems, Inc. Bulletin, "What do HVAC odor/corrosion control systems and easy maintenance have in common?" (Before Dec. 1992).

Extraction Systems, Inc. Brochure for HECCA–HEPA filter (Before Dec. 1992).

Foss Brochure "Engineered Nonwoven Fabrics" (Before Dec. 1992).

Brochure "Nanosorb™ 101–20 Activated Carbon Pad" (Before Dec. 1992).

Brochure, Lewcott Corp., "Activfilter Activated Carbon Impregnated Media New Technology for Removal of Odors, Contaminants, Pollutants and Irritants" (Before Dec. 1992).

Kinkead, "Controlling A Killer: How To Win The War Over Gaseous Contaminants", reprinted from CleanRooms Magazine, Jun. 1993.

Kinkead, "National Archives II Performance Evaluation", Extraction Systems, Inc. (Representative Memo –dated Oct. 3, 1991).

Kinkead, "Downstream carbon loss from DPCC Adsorbers", Extraction Systems, Inc., (Product Information Release dated Sep. 18, 1991).

Kinkead, "Museum Literature, MNR Test Results, IAQ Act", Extraction systems, Inc. (Memo dated Nov. 15, 1990).

Kinkead et al., "Targeting Gaseous Contaminants in Wafer Fabs: Fugitive Amines", Microcontamination, pp. 37–40 (1993).

Stevie, et al., "Boron contamination of surfaces in silicon microelectronics processing: characterization and causes", *J. Vac. Sci. A.*, 9(5):2813 (1991).

Muller, et al., "Detection and Sources of Volatile Clean Room Contaminants", Viewgraphs, IES Meeting (1993).

MacDonald et al., "Airborne Chemical Contamination of a Chemically Amplified Resist", *SPIE* 1466:2–12 (1991).

Mori et al., "Correlating Organophosphorus Contamination On Wafer Surfaces with Hepa–Filter Installation", *Microcontamination*, pp. 35–38 (1992).

"VaporSorb® Effects On Wafer Surface Properties", Extraction Systems, Inc.

Jensen, "Ultraclean Manufacturing Technology State of The Industry Address", Microcontamination Conference '92.

Suzuki et al., "Gas Adsorption on Wafers", *Microelectronics Manufacturing Technology* pp. 38–41 (1991).

"Odor and Corrosion Control," Extraction Systems 1993 catalog.

Letter to potential client (Jan. 1992).

| PROCESSING STATION | CONTAMINANTS | ACTIVATED CARBON FILTER IMPREGNATE |
|---|---|---|
| Photolithography | amines, bases, bacterial | $ZnCl_2$, $H_2SO_4$, or citric acid and KI or Ag-containing compound (KOH) |
| Etch | acids | KOH + KI, KOH + $K_2CO_3$, or KOH + $Na_2CO_3$ KOH + NaOH |
| Chemical Vapor Deposition | amines, organic vapors | $ZnCl_2$, $H_2SO_4$, or citric acid (KOH) |
| Thin Film Deposition | organic vapors | (KOH) |
| Developing | bases | $ZnCl_2$, $H_2SO_4$, or citric acid (KOH) |
| Diffusion | acids | KOH + KI, KOH + $K_2CO_3$, or KOH + $Na_2CO_3$ KOH + NaOH |
| Epitaxy | amines, acids | $ZnCl_2$, $H_2SO_4$, or citric acid and KOH + KI, KOH + $K_2CO_3$, or KOH + $Na_2CO_3$ KOH + NaOH |

Fig. 7

CLEAN ROOM AIR FILTERING

CROSS REFERENCE TO RELATED APPLICATIONS

This application is a continuation-in-part of application U.S. Ser. No. 07/807,151 filed Dec. 13, 1991, now abandoned which is a continuation-in-part of abandoned application U.S. Ser. No. 07/283,318 filed Dec. 12, 1988.

BACKGROUND OF THE INVENTION

This invention relates to air filtering inside clean rooms.

Air filtering is critical in the manufacture of semiconductor devices. Tremendous efforts are made to eliminate contaminants from the semiconductor device manufacturing site, commonly referred to as a clean room. Clean room contaminants may be generally classified as either particulate or gas-phase. Common particulate contaminants include dust, lint and other debris. Examples of gas-phase contaminants, which are dimensionally 30,000–40,000 times smaller than particulate contaminants, include acid gases, base gases including ammonia and other reactive amines, volatile organic compounds (VOCs), and boron.

Until recently, most of the efforts in clean room design have focused on removing particulate contaminants, which were viewed as having the most impact on device yields and device performance. However, it has been discovered that gaseous contamination is an important limiting factor in the further reduction of device geometry and the improvement of device performance.

Attempts have been made to reduce gas-phase contamination by incorporating traditional rack and tray type gas-phase filters into existing cleanroom air handling systems. A rack and tray filter generally includes a perforated metal structure which contains loose sorbent particles. Because rack and tray filters tend to generate large quantities of particulate contamination (due, at least in part, to the vibration of air handling systems), additional particulate filters, preceding a final high-efficiency particulate air (HEPA) filter, are required downstream from the rack and tray system. These additional particulate filters require frequent servicing due to accumulation of particles in the filters.

One cleanroom design scheme to reduce gas-phase contamination involves isolating the process stations which generate particular contaminants from those processes which are sensitive to those contaminants (e.g., by constructing barriers between stations, or by increasing the distance separating individual processing stations). Such solutions have affected capital cost and work flow efficiency.

Boron is a particularly troublesome gas-phase contaminant which is found naturally in the air as boric acid, and is given off by borosilicate glass in the high efficiency particulate air (HEPA) filters commonly used in clean room air recirculating systems. Reduction of semiconductor device yields has been traced to relatively low levels of boron contamination which causes counter-doping of lightly doped n-type layers. Since the atmosphere and the HEPA filters are sources of boron contamination, it has been viewed as impractical to remove boron from the clean room air. Instead, process engineers accept boron contamination as inevitable and typically add an additional cleaning step (a buffered HF clean/etch) to reduce the level of boron on the wafer surface. Alternatively, process engineers may simply modify the required doping levels to compensate for the doping effect of boron.

SUMMARY

In one aspect, the invention features a clean room that has an air handling system for introducing air into the clean room from a source containing a predetermined gas-phase contaminant. The air handling system comprises the combination of a HEPA filter (high efficiency particulate air filter), and directly upstream thereof a chemical filter of the pleated filter type comprising an air permeable, relatively thick web of non-woven fibrous carrier material of pleated form. The web includes a matrix formed of a large multiplicity of synthetic fibers and is characterized in that activated carbon particles are distributed throughout the web, bound in the interstices of the matrix in a manner preventing loss to the air of particles in quantity substantially detrimental to the performance of the HEPA filter. The activated carbon particles are of the type selected to remove the predetermined gas-phase contaminant from the air from the source.

Because the particles are suspended in a fiber web, smaller particles may be used in a filter according to the invention as compared to the particles that can be used in conventional rack and tray systems. Rack and tray systems require large particles in order to provide inter-spatial passages for air streams to flow through. In rack and tray designs, the complete surface of each activated carbon particle is not exposed to the air streams. The use of smaller particles which have surfaces completely exposed to the air streams allows the filters of the invention to achieve the same filtering functionality as rack and tray designs, with only a fraction of the weight of activated carbon. This is because gas-phase filtration, for low concentrations of gas-phase contaminants, depends upon the surface area of the activated carbon surface that is exposed to the air streams. For example, a twenty-six pound activated carbon filter according to the invention achieves the same functionality of low concentration gas-phase filtration as a two-hundred and forty pound rack and tray filter for similar clean room air streams.

The clean room preferably includes a processing station that generates a gas-phase contaminant. The air handling system preferably comprises a recirculating air system in which air from adjacent the processing station comprises the source of air for the air handling system. The activated carbon particles are preferably selected to remove the contaminant produced by the processing station.

The air handling system preferably includes a make-up air system for drawing air from an atmosphere outside of the clean room, subject to contamination by an ambient contaminant. The activated carbon particles are preferably selected to remove the ambient contaminant.

The activated carbon particles preferably carry a reactant that is selected to react with the gas-phase contaminant to produce a product that is bound upon the activated carbon particles.

For example, the source of air for the air handling system typically includes air that has previously passed through borosilicate filter material exposed to acid etchants and the activated carbon particles preferably carry a basic substance reactant with free boron in the air (e.g., KOH) with a concentration of 8% by weight, or greater.

The source of air for the air handling system typically also comprises air that has previously passed through carbon filter material exposed to photoresistant compounds and the activated carbon particles would preferably carry an antibacterial compound (e.g., potassium iodide or a compound comprising silver).

The source of air for the air handling system may comprise air containing acid gases and the activated carbon particles would preferably carry a base compound (e.g., a compound selected from the group consisting of KOH, KI, $K_2CO_3$, $Na_2CO_3$ and combinations thereof).

The source of air for the air handling system may also comprise air containing amines or bases and the activated carbon particles would preferably carry an acid compound (e.g., a compound selected from the group consisting of $H_2SO_4$, $ZnCl_2$ and citric acid).

The source of air for the air handling system may comprise air containing monovalent and divalent cations and the activated carbon particles would preferably carry a chelating compound (e.g., an ion exchange resin or chelating agent such as choline).

In general, in another aspect, the invention features a clean room in which the chemical filter is formed from a multiple layer web including a top layer that has an original fiber density and a bottom layer that has a second fiber density greater than the first fiber density.

The web is preferably exposed to infrared energy by directing a source of first infrared energy at the top surface of the web, and directing a source of a higher infrared energy at the bottom surface of the web. The activated carbon particles preferably range in U.S. mesh size 20×140.

The chemical filter is further characterized, in operation, as losing to the air, no more than 100,000 particles per cubic foot of air and producing no more than 0.8 inches W.G. (200 Pa) of pressure drop to the air flow when the air is flowing at 2000 cubic feet per minute through a filter of four square foot area.

In another aspect, the invention features a chemical filter of the pleated filter type being the product of the process of introducing the activated carbon particles from a fluidized bed onto the top surface of the top layer, agitating the web in a manner that causes the adsorbent particles to enter the thickness of the web and reach a resting place depending upon particle size (the smaller the particle size, on average, the deeper the entry into the thickness of the web), exposing the web to infrared energy in such a manner that the particles become heated, and calendering the web in a manner that substantially preserves the filtering capability of the adsorbent particles, thereby causing the adsorbent particles to become bound in the non-woven fibrous carrier material in the size-distributed manner.

In another aspect, the invention features a chemical filter of the pleated filter type for improving the filtration of airstreams inside an air handling system of an existing clean room having high-efficiency particulate air (HEPA) filters. The filter comprises a web of thermo-plastic fibers that has edges that are potted inside a casing formed from material of low vapor pressure so that the casing does not contribute gas-phase contamination to the existing clean room. The chemical filter is retro-fitted inside the air handling system of the existing clean room directly upstream of the HEPA filters. The filter includes particles bound to the thermoplastic fibers in a manner preventing loss to the air of particles in quantity substantially detrimental to the performance of the HEPA filters. The chemical filter is arranged so that the relatively closed surface is directed toward the HEPA filters.

Chemical filters employed directly upstream of the HEPA filters inside the recirculating air systems of a clean room, without additional intervening particulate filters, allows for efficient gas-phase filtration, with a lower pressure drop, while only requiring a small amount of clean room space.

Employing filters targeted for the removal of the specific contaminants contained in the various air streams inside a clean room, substantially reduces gas-phase contamination, thereby increasing device yields and process reliability. While matching the removal capabilities of the individual filter systems within the clean room substantially reduces self-contamination and cross-contamination of the processing stations, without having to resort to physically isolating the processing stations, thereby permitting the clean room to be designed according to work flow, rather than contaminant, considerations.

The effective gas-phase purification of the air streams inside a clean room reduces the following problems typically encountered in a clean room environment: process equipment downtime, odors, corrosion of capital equipment, wafer hazing, the effects of chemical spills, and the exposure of workers to gas-phase chemicals.

Effective gas-phase filtration also eliminates process degradation that affects the electrical properties of fabricated devices. For example, VOCs can cause changes in barrier height, contact resistance and surface charge in semiconductor devices.

Other advantages and features will become apparent from the following description and from the claims.

DESCRIPTION

STRUCTURE

Figure 1A:
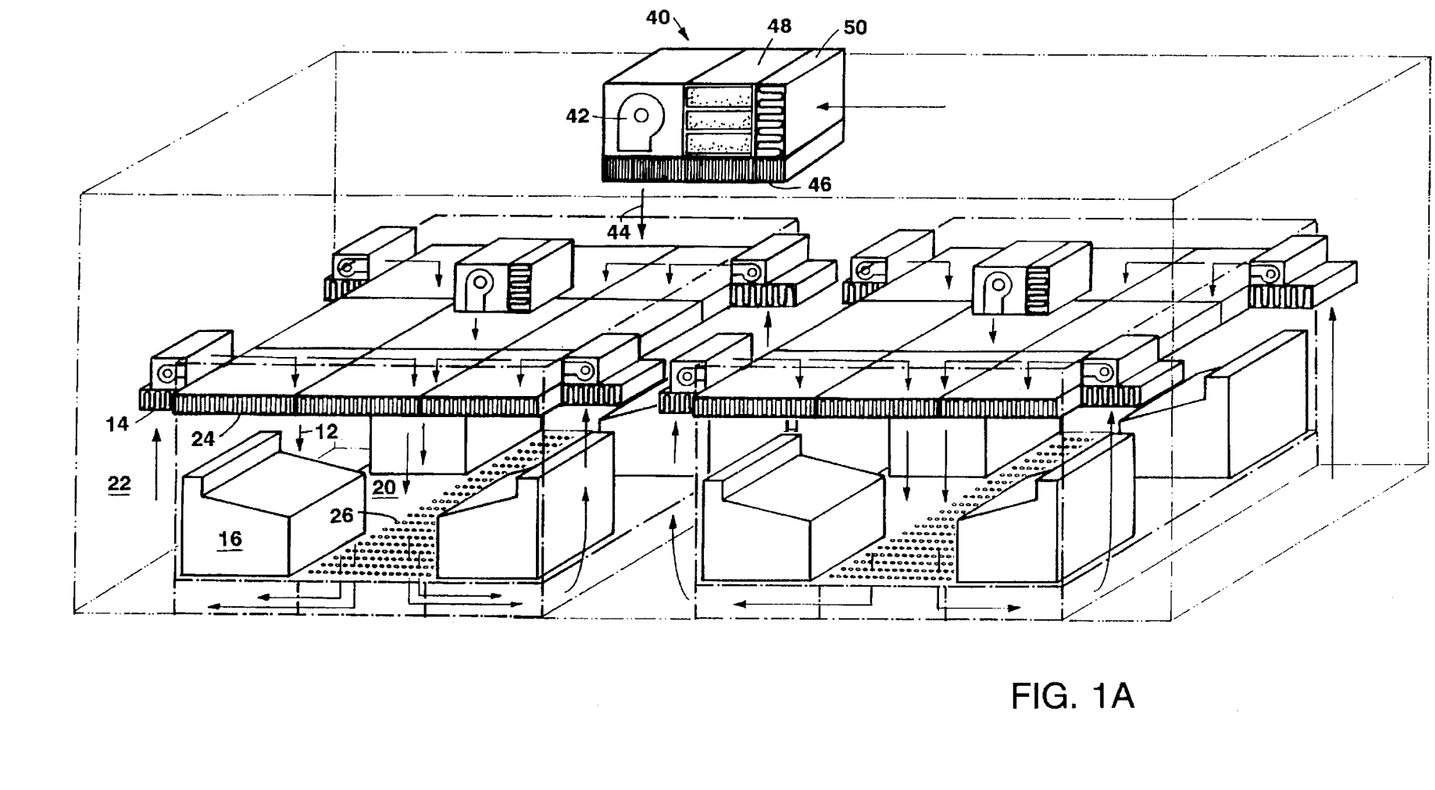
FIGS. 1A–1C are schematic perspective, side, and top views of a clean room according to the invention.
Figure 1B:
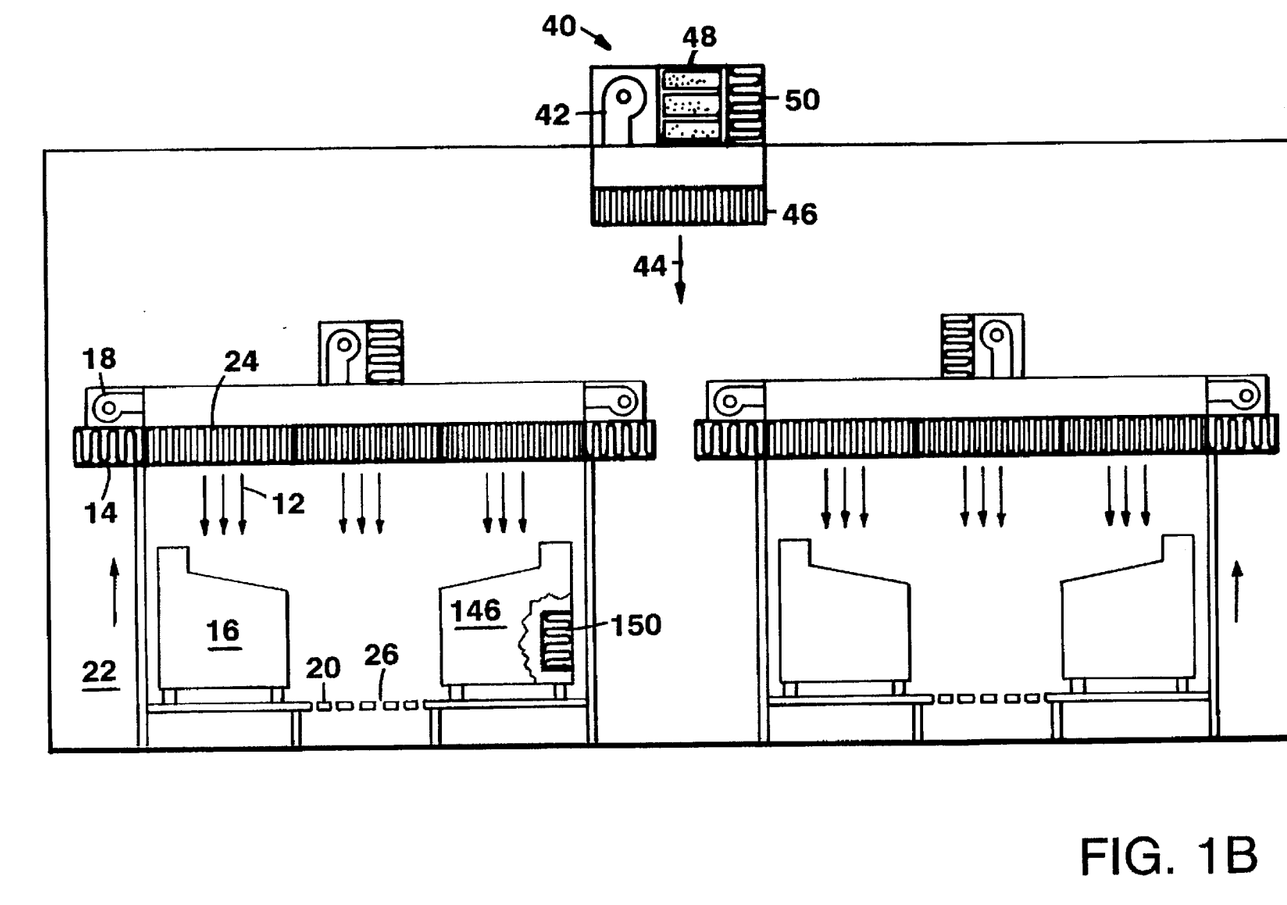
Figure 1C:
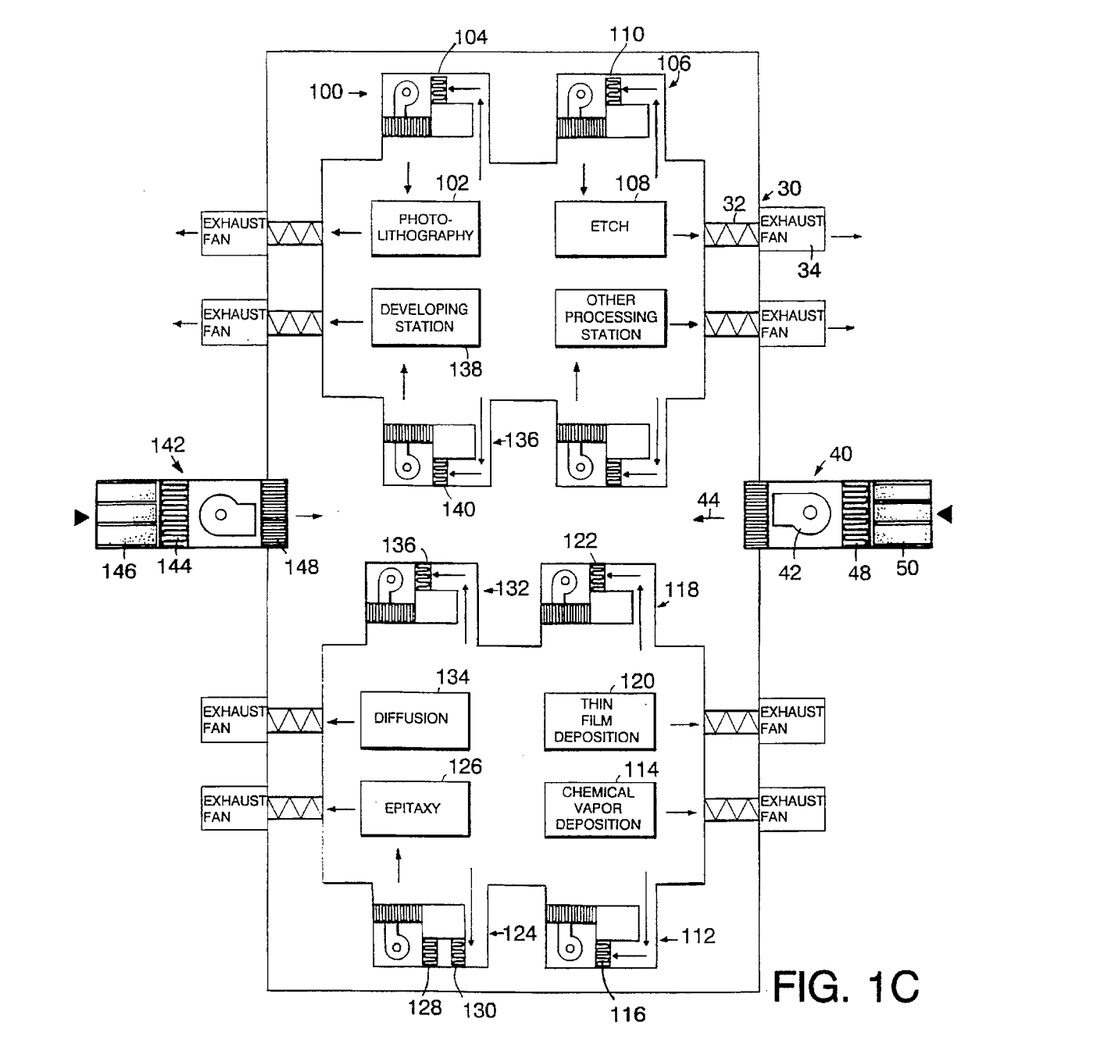

Referring to FIGS. 1A–1C, gas-phase contaminants (too small to be shown) in recirculating air streams 12 are removed by gas-phase chemical filters 14 in a manner which reduces both self-contamination and cross-contamination of process stations 16 (e.g., conventional semiconductor photolithography, etch, chemical vapor deposition, thin film deposition, developing, epitaxy and diffusion stations). Gas-phase contaminants are released into the recirculating air streams by process stations 16.

Each processing station 16 is associated with a recirculating air handling system that generates recirculating air streams 12 (e.g., with conventional air blowers 18). An air stream 12 follows a path which includes, a process station 16, a floor 20, a common air plenum 22, a gas-phase filter 14, and a high efficiency particulate air (HEPA) filter 24 which is used to remove particulate contamination (e.g., dust, lint, and other debris) from the air stream. The floor 20 is a conventional clean room floor that has air passages 26 to allow air streams 12 to pass through.

The air stream recirculation rate is on the order of 10 interchanges per minute, allowing a thorough filtering of the air streams even when the gas-phase filters are near the end of their service life (i.e., when the filters have a low efficiency, defined by the formula (X-Y)/X wherein X is the upstream concentration of pollutant, and Y is the downstream concentration of pollutant). A higher recirculation rate can compensate for the inevitable decrease in filter efficiency. For example, after 10 air cycles a filter with a 30% efficiency may reduce the level of air contamination by 99%.

Each processing station 16 is also associated with an exhaust system 30 (FIG. 1C) that includes a filtration unit 32 (e.g., chemical air scrubbers) and an exhaust fan 34. The exhaust systems remove air from inside the cleanroom, near their associated processing stations, to an area outside the clean room.

Make-up air handling system 40 is used to replace the air removed from the clean room by the exhaust systems with air from outside the clean room. Air blower 42 generates the make-up air stream 44. A HEPA filter 46 is located downstream of the blower to prevent fine particulate contaminants from entering the clean room common air plenum 22. An efficient (about 70% efficiency) particulate bag filter 48 is located upstream of the HEPA filter to prevent loading of the HEPA filter. A pre-filter 50, which generally has a particulate removal efficiency of 30%, is located at an inlet port of the make-up air handling system for preventing premature loading of the bag and HEPA filters.

In the design of the recirculating and make-up air handling systems it is desirable to achieve the lowest practical level of particulate and gas-phase contamination possible. However, a compromise must be reached between level of contamination and the cost of the clean room.

To achieve the lowest practical level of air contamination additional air filters could be added in series to all of the air handling systems. However, this would add to the total cost of the clean room in two ways. First, additional filters would cause an increase in pressure drop (i.e., resulting in reduction in the volume of air per unit time flowing in air stream 12 through filter 14) in the air handling systems and larger air blowers would be required to make up the loss in pressure. Second, the increase in the size of the blowers and the additional space taken up by the additional filters would require a larger and therefore more expensive clean room. Filters Conventionally, it has been very difficult to install gas-phase filtration equipment inside the recirculating air systems of clean rooms. The large size of conventional chemical air filters made them difficult to be retro-fitted inside existing clean rooms, and made them more costly to design.

Figure 2:
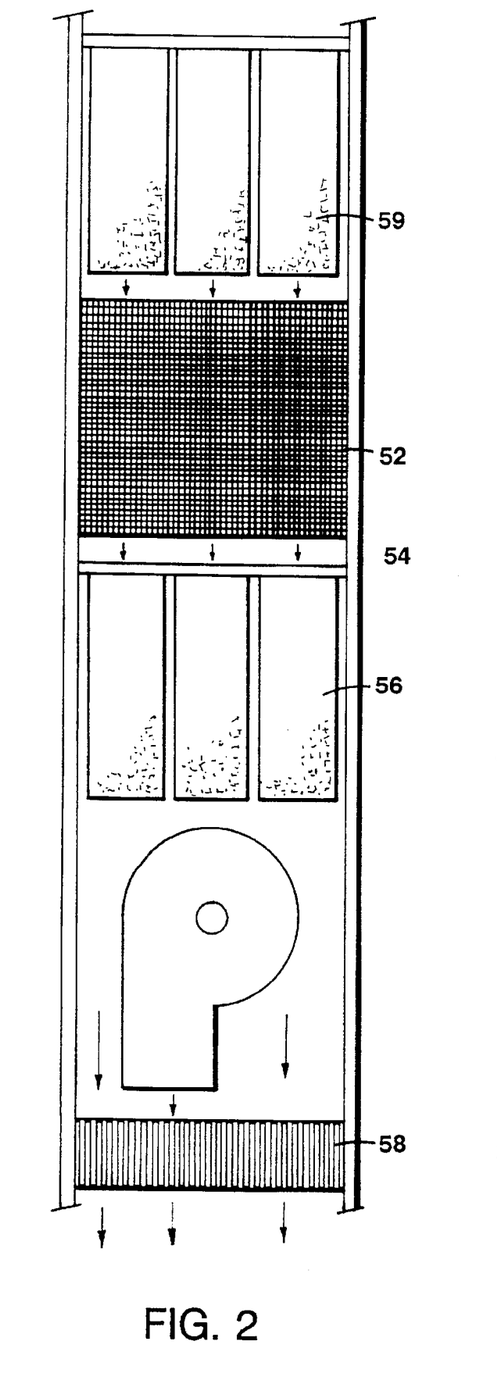
FIG. 2 is a schematic side view of a conventional clean room air handling system.

FIG. 2 shows a conventional rack and tray filter system 52, with typical dimensions of 24 inches by 24 inches in face area by 29 inches in depth. The sorbent material is contained within a perforated metal container that tends to give off a relatively high concentration of particulate material into the air streams 54 of the air handling system. Accordingly, a filter 56 (e.g., a bag filter) is located downstream of the rack and tray system 52 to capture the released particulate matter and to prevent the rapid loading of the HEPA filter 58, which are expensive and difficult to replace. In preferred embodiments an additional filter 59 is employed directly upstream of the rack and tray filter 52 to remove particulates from the air streams which would tend to cover the sorbent surfaces of the rack and tray filter, rendering them unavailable to the air streams.

The use of four filters in series (i.e., the particulate filter, the rack and tray filter, the pre-filter and the HEPA filter) add pressure drop (i.e., a reduction in the volume of air per unit time flowing in the air stream 12) and add to the size of the air handling system, both significant increasing the costs associated with the construction of the clean room. Additionally, the maintenance associated with rack and tray systems (e.g., emptying the trays of the sorbent and filling the trays with fresh sorbent material) is also very expensive and time consuming, adding to clean room down-time costs, and adding particulate contaminants to the clean room air streams.

Figure 3:
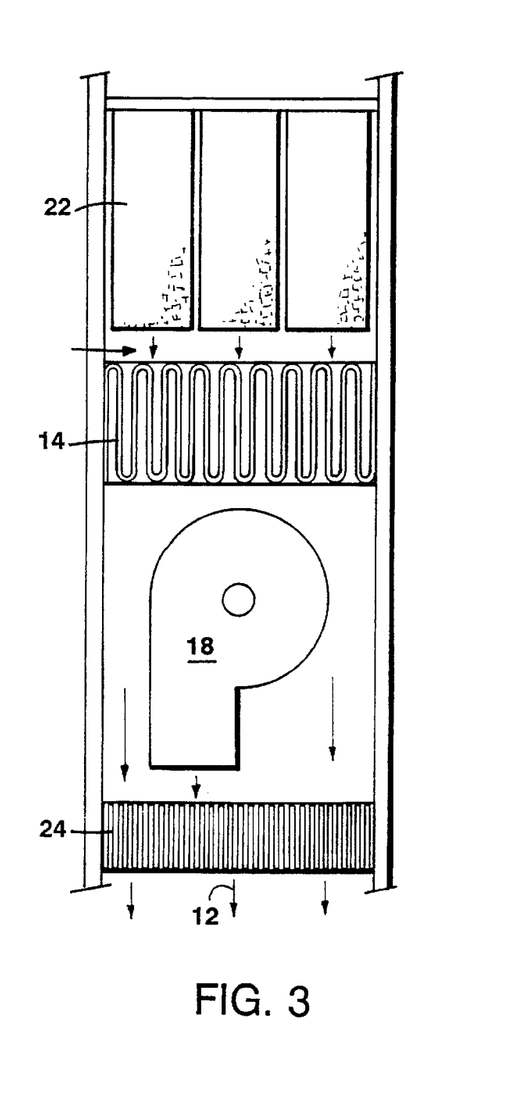
FIG. 3 is a schematic side view of an air handling system of the invention.

Referring to FIG. 3, a gas-phase filter 14 according to the invention is located directly upstream of the HEPA filter 24 (i.e., there is no intervening filter between the HEPA filter and the chemical filter that would cause additional pressure drop to the air stream) inside the recirculating air systems of the clean room. In a preferred embodiment, a particulate bag filter 60 is positioned directly upstream of chemical filters 14 to remove particulates from the air streams which would tend to cover the sorbent surfaces of the chemical filters rendering them unavailable to the air streams.

Figure 4:
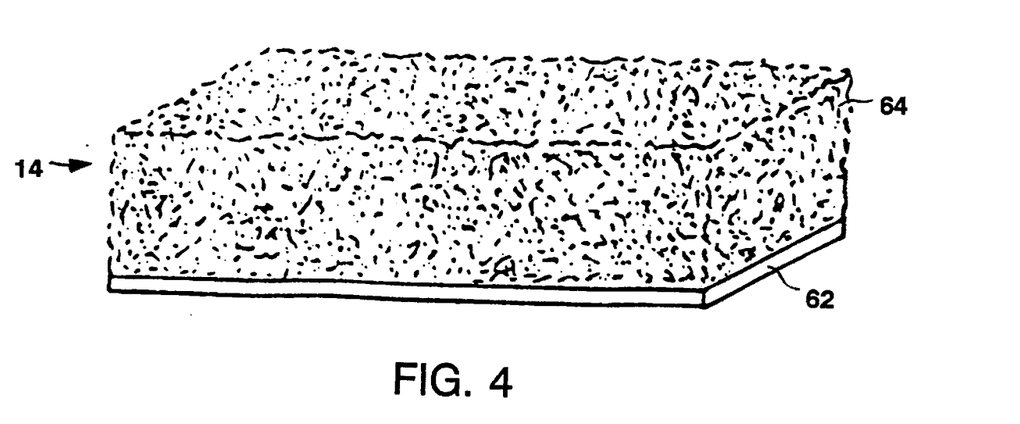
FIG. 4 is a perspective view of an original filter material before heating and calendering.

As shown in FIG. 4, each gas-phase filter 14 originally comprises a dense non-woven backing 62 that is preferably a polyester batting, or some other thermo-plastic material, with a denier in the range of about 15 denier which is needled, thereby increasing its density by concentrating and reducing the initial thickness to a final thickness of approximately 0.25 inch. The material is then spray bonded to a loose non-woven polyester batting 64 of approximately 6 denier having a thickness of approximately 1 inch. The resulting polyester batting has two distinct layers and a thickness of approximately 0.8 inch.

Alternatively, the non-woven carrier may comprise a polyester batting which is needled on one side thereby forming a single polyester batting having a dense layer on one side and a total thickness of about 0.8 inch.

Adsorbent particles are evenly distributed throughout the polyester batting. An example of an adsorbent particle includes but is not limited to activated carbon which is chemically impregnated and retains its reactive and adsorptive capacity as a result of the dry processing, described in detail below.

Alternatively, the adsorbent particles may be ion exchange resins.

Overall, the dry processing of the non-woven polyester batting, which includes the combination of the fluidized bed carbon deposition process, the inherent stratification of the batting's density, and the even distribution of the carbon particles as well as the stratification of the carbon particle size, allows for a fabric architecture having an increased bed depth at a very low pressure drop, which is highly desirable due to its high first pass efficiency coupled with its low operating cost.

Figure 5:
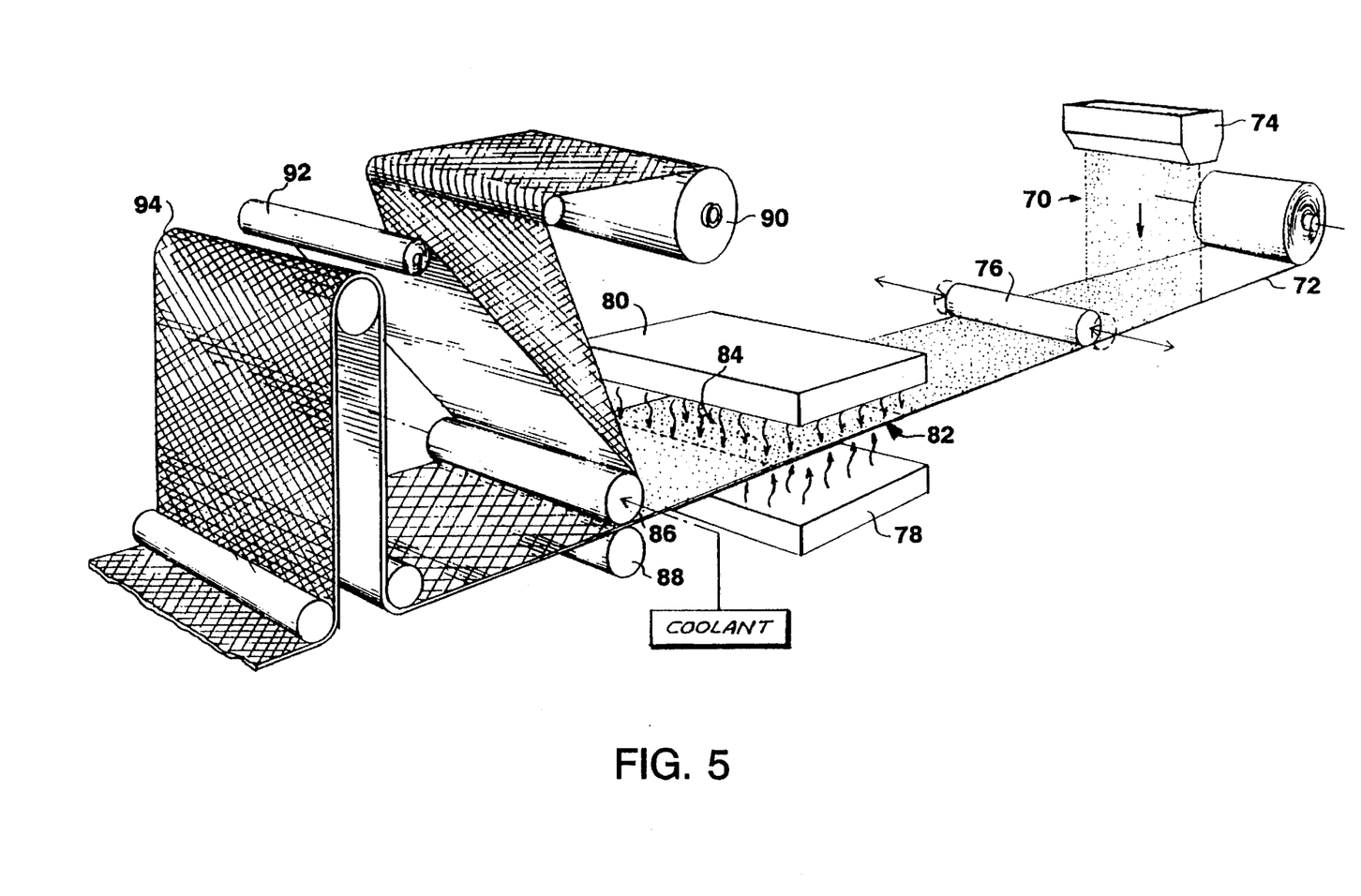
FIG. 5 is a perspective view of a filter manufacturing process according to the invention.

As shown in FIG. 5, the adsorbent particles 70 are poured onto a polyester batting 72 from a fluidized bed 74, the batting 72 is agitated using a roll bar 76 which agitates in a direction which is perpendicular to the length of the batting. This agitation insures that the carbon particles 70 ranging in U.S. mesh size from 20×50 to 30×140 are evenly stratified throughout the depth of the batting 72. The agitation causes the smaller particles to migrate furthest from the batting surface while the larger particles remain nearer the surface thereby providing a stratification of the carbon particles throughout the depth of the polyester batting. An increased bed depth of adsorbent distributed throughout the batting is highly desirable as it increases residence time, increases exposure of the adsorbent particle surfaces, provides a low pressure drop, as well as substantially increases the lifetime of the filter.

The adsorbent particles 70, distributed in the batting 72, are then heated, preferably using two zones 78, 80 of radiant infrared energy at different temperatures. In the first zone 78, the temperature is set higher and directed toward the dense non-woven backing 82 of the composite to insure that heat energy penetrates deep within the dense backing. In the second zone 80, the temperature is lower as it is easier for radiant heat energy to penetrate the loose non-woven surface 84. The adsorbent particles are heated to an overall average temperature of about 250°–350° F.

Using infrared energy that is not substantially absorbed by the fibers of the batting, and is instead, preferentially absorbed by the adsorbent particles, which act as black-body absorbers, causes the adsorbent particles to adhere to the batting at points where the particles contact the batting. This procedure avoids the necessity of raising the temperature of the entire batting to a point at, or near, the melting point of the polyester batting, which could cause the batting to melt and collapse thereby encasing the particles and destroying their chemical activity.

The batting 72 is then calendered using a pair of calender rolls 86, 88. The first of these rolls 86 can be temperature-controlled which allows the heating and calendering steps to be carried out at a steady temperature of around 110°–115° F., and prevents overheating and subsequent melting of a cover sheet 92 that may be provided over the backing layer 82, and prevents over-calendering of the batting.

Furthermore, when the temperature-controlled roller 86 is used, the pressure at which the batting is calendered can be lowered from 3000–5000 psi to under 1000 psi as a result of the steady temperature maintained during calendering. Higher calendering pressures can crush the particles particularly when those particles are chemically impregnated carbon particles, thereby forming dust, which cannot be retained in the filter composite. Therefore, the ability to use lower pressures in the calendering step is very desirable in preventing the destruction of the carbon particles contained in the batting, and formation of carbon dust.

In addition, a non-woven cover sheet 92, which helps to maintain the carbon in the batting, may be calendered with the batting 72, as discussed above.

If desired the composite may be pleated using machines common to the air filter industry. The pleated structure may be placed in a containment structure such that the crease of the fold is perpendicular to the air flow. If the filter material is to be pleated a wire mesh 80 may be calendered with the batting. The wire mesh 90 helps maintain the filter material in a pleated configuration. The presence of the wire mesh 90 in the filter material also enables the filter material to be embossed before pleating. Embossing a material before pleating is a known technique in the industry.

Optionally, the material may be conducted over an upper roller 94 to facilitate cooling the material prior to further processing.

Figure 6:
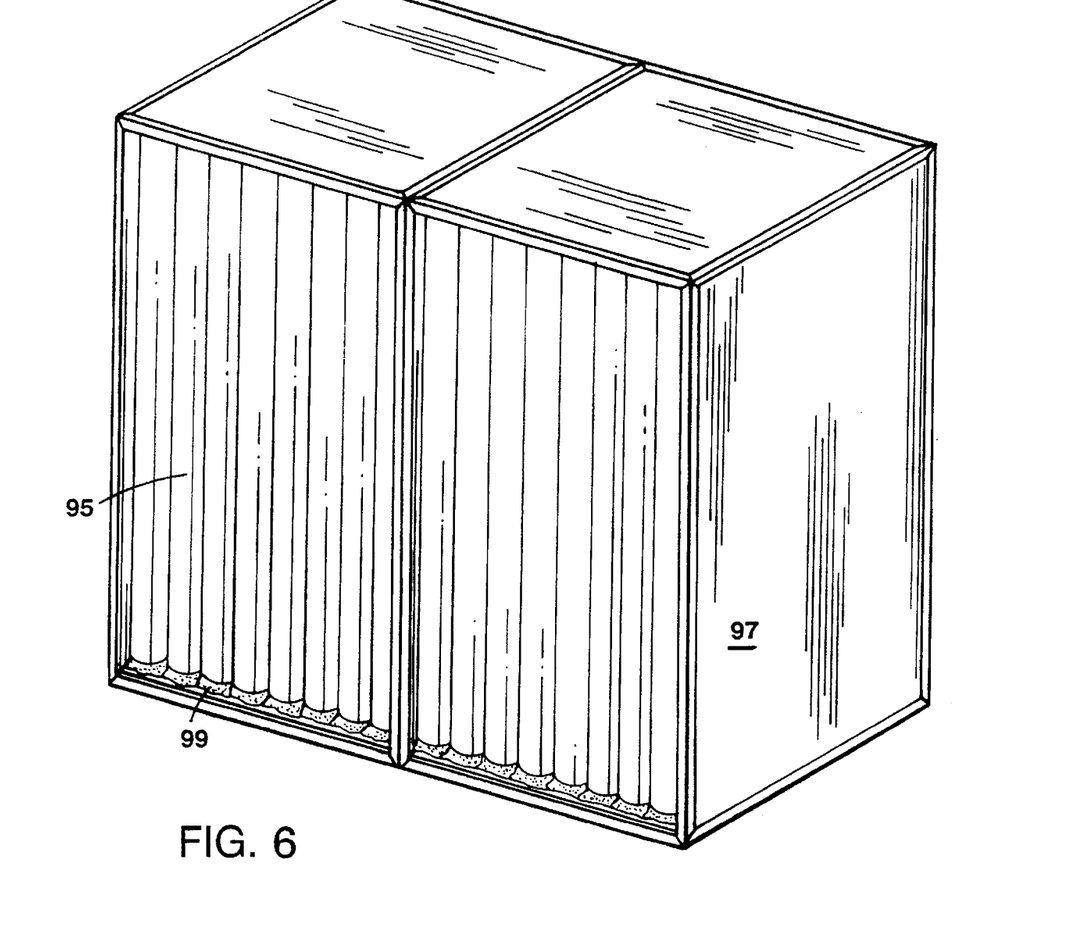
FIG. 6 is a perspective view of a filter of the invention potted within a hardboard casing.

In a preferred embodiment, pleated filter structure 95 is framed within a formaldehyde-free prelaminate-coated hardboard (e.g., Masonite™ casing 97 with dimensions of 24 inches by 12 inches in face area by 12 inches in depth, as shown in FIG. 6. This size permits two filters seated side-by-side, as shown, with a combined face area of 24 inches by 24 inches, to be easily retro-fitted into conventional clean room air handling systems. The materials chosen for the construction of casing 97 are chosen to have a low vapor pressure so that the casing does not contribute gas-phase contamination to the clean room.

The filter is potted inside the casing so that the higher density fibers are downstream the lower density fibers. In this configuration, any larger carbon particles that may become unbound from the lower density fibers will be caught by the downstream higher density fibers. The ends of the pleated structure are potted into the casing with a foamed polyamide hot-melt adhesive film. The polyamide adhesive and the formaldehyde-free casing are selected because they do not off-gas into the clean room after they have been installed. The two end flaps, which would normally be loose in conventional pleated structures, are also sealed using the same polyamide adhesive. The filter and frame form a single disposable filter unit.

Targeted Filtering

Gas-phase air contaminants are actually collections of molecules unlike particulate contaminants and are best distinguished from particulates by size. Very small particulate matter may be about 0.12 microns in diameter, while gas-phase contaminants are typically only a fraction of an angstrom in diameter (i.e. about 30,000–40,000 times smaller). This size differential translates into entirely different removal mechanisms for gas-phase and particulate contaminants. Two common gas-phase contaminant removal techniques are adsorption/condensation and chemisorption.

Adsorption/condensation first involves the attachment of a gas or vapor to the surface of a sorbent (i.e. a granulated material capable of adsorption). Unlike particulate matter, gas-phase air pollutants possess specific chemical and physical properties unique to the chemical specie they represent. The boiling point, vapor pressure, and reactivity characteristics of the gas-phase pollutants are especially important in the design of gas-phase air purification equipment. Generally, gas-phase contaminants with a boiling point of 100° C. or greater may be effectively removed using activated carbon alone, while removal of contaminants with lower boiling points requires some sort of chemisorption mechanism (e.g., chemically treated activated carbon).

Sorbent-based filters operate on the principle of diffusion which brings the pollutant to the sorbent surface and provides the mechanism by which the pollutant penetrates the exterior surface of the sorbent material. The resistance to the diffusion of the gas-phase contaminant is known as mass transfer resistance.

Filters 14 provide high mass transfer area (low mass transfer resistance) with respect to the chemical impregnate by using micro-metric particles (e.g., 20 by 140 mesh (U.S.)), which are about one tenth of the size of the particles used in conventional rack and tray systems. Activated carbon acts as an optimal media to suspend a chemical reagent via impregnation, and it also adsorbs organic vapors. The pleated construction of the filter reduces air flow resistance compared with conventional rack and tray systems. The suspension of the micro-metric carbon particles provides very high reagent utilization at very low pressure drops.

These filters contribute one tenth the level of particulate loading of conventional bag filters (i.e., they contribute less than 10,000 particles per cubic foot of air in air streams of 2000 cubic feet per minute passed through filters with a face area of 24 inches by 24 inches and with a depth of 12 inches), allowing the filters to be employed upstream of HEPA filters without requiring additional filters therebetween. The small size, relative to conventional rack and tray systems, and the low particulate contribution of these filters allows them to be retro-fitted in existing clean rooms, as well as to be installed in new clean room air handling systems at a lower cost than with conventional rack-and-tray systems.

The first step in the design of the clean room is to identify the gas-phase contaminants released into the air streams, as well as the source of the contaminants. Once the contaminants have been identified, the gas-phase filters can be treated with impregnates according to the following examples and then located in the appropriate air streams. Activated carbon is impregnated by solubilizing the impregnate in a water medium, which is then sprayed onto the surface of the carbon particles for a period of time depending on the level of impregnation required (typically 1–70% by weight).

It should be noted that in the cases where the various impregnate chemistries are not compatible for use on the same filter (e.g., combining acids and bases), additional filters can be employed in series.

EXAMPLE 1

To remove organic vapors from an air stream, un-impregnated coconut shell, or coal-based, activated carbon is used.

EXAMPLE 2

To remove acid gases from an air stream, an activated carbon filter is impregnated with a chemical from the following group: KOH, KI, $K_2CO_3$, NaOH, and $Na_2CO_3$.

EXAMPLE 3

To remove ammonia and other amines from an air stream, an activated carbon filter is impregnated with either $H_2SO_4$, $ZnCl_2$, or citric acid.

EXAMPLE 4

Gas-phase contaminants 10 may occur naturally in the air streams, or can be released from the filtration system. For example, boron contamination can be released from borosilicate glass used in the manufacture of HEPA filters. One release mechanism occurs when fluorine gas (e.g., released from an etching process) in the presence of water (e.g., from moisture in the air) etches the borosilicate glass, releasing a gas-phase silicon boride.

Boron, as well as fluorine, gas-phase contamination is removed from the air streams by impregnating the activated carbon filters with potassium hydroxide or some other low vapor pressure base. It has been discovered that boron may be efficiently removed from air streams by impregnating the activated carbon in the air filters with KOH at concentrations of 8% by weight, or greater.

EXAMPLE 5

Bacteria may also interfere with clean room processing. Bacteria growth may be promoted when novolak-based photoresist compounds adhere to the activated carbon inside the filters of the clean room air handling system, forming lactose. Accordingly, activated carbon filters, particularly those associated with photolithography stations, are impregnated with antibacterial agents, such as potassium iodide and silver compounds, to suppress the growth of bacteria.

EXAMPLE 6

The gas-phase contaminants may also comprise monovalent and divalent cations. For example, sodium and calcium cations are both major contributors to site defects on semiconductor wafer surfaces. Activated carbon filters impregnated with chelating agents (e.g., an ion exchange resin or chelating agent such as choline) are used to remove these contaminants.

Clean Room Design

Figure 7:
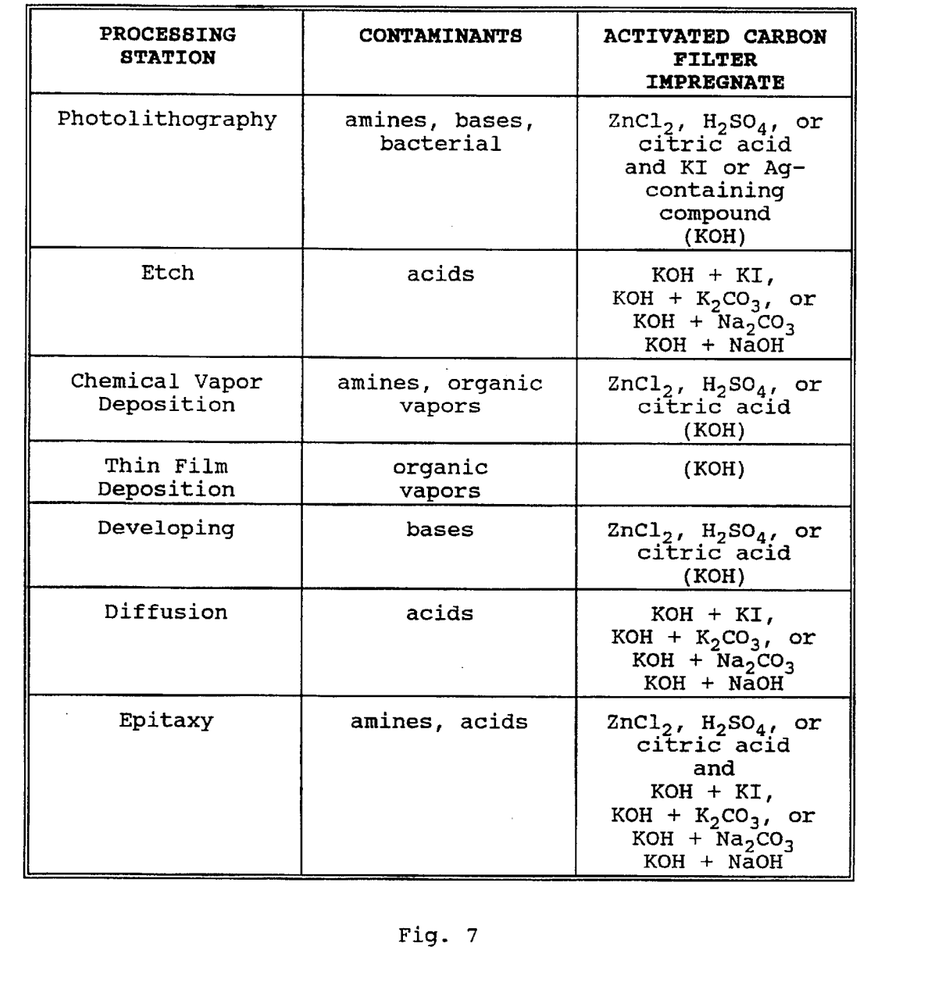
FIG. 7 is a table associating gas-phase filter impregnates with process stations of a clean room.

The gas-phase filters, located in the air handling systems associated with each processing station, are chemically impregnated to remove gas-phase contaminants that are likely to be released into its air stream. The table shown in FIG. 7, summarizes the processing stations inside the clean room, the major contaminants the processing station releases into an air stream, and the chemical impregnate used to remove the released contaminants.

As shown in FIGS. 1A–1C, the processing stations inside the clean room may be located proximally without suffering the effects of cross-contamination.

Referring to FIG. 1C, air handling system 100, associated with a photolithography station 102, includes an activated charcoal filter 104 impregnated with zinc chloride and potassium iodide. Air handling system 106, associated with an etch processing station 108, includes an activated charcoal filter 110 impregnated with potassium hydroxide and potassium carbonate. Air handling system 112, associated with a chemical vapor deposition station 114, includes an activated charcoal filter 116 impregnated with zinc chloride. Air handling system 118, associated with a thin film deposition processing station 120, includes an activated charcoal filter 122. Air handling system 124, associated with an epitaxy processing station 126, includes a first activated charcoal filter 128 impregnated with zinc chloride and a second activated charcoal filter 130 impregnated with potassium hydroxide and potassium iodide. Air handling system 132, associated with a diffusion processing station 134, includes an activated charcoal filter 136 impregnated with potassium hydroxide and sodium carbonate. Air handling system 136, associated with developing station 138, includes an activated charcoal filter 140 impregnated with zinc chloride or sulfuric acid.

Other embodiments are within the scope of the claims.

For example, an activated carbon filter impregnated with potassium hydroxide may be located in the path of each air stream for removing boron-containing gas-phase contamination, as indicated in the table of FIG. 7 by "(KOH)" in the activated carbon filter impregnate column.

A conventional semiconductor clean room may be retrofitted with the activated carbon chemical air filters of the invention.

Instead of using conventional pre-filters in make-up air handling system 142 (FIG. 1C), a chemically impregnated activated carbon filter 144 is used in series with a conventional bag or pleated filter 146 and a HEPA filter 148.

An activated carbon chemical filter, treated with an appropriate impregnate, may be installed inside processing stations that have independent air handling systems.

What is claimed is:

1. An air filtering system for filtering an air stream for use in a clean room comprising
    a HEPA (high efficiency particulate air) filter positioned to introduce air into the clean room and comprising borosilicate glass, and
    an upstream air filtering bed positioned upstream of said HEPA filter to receive from the clean room an air stream containing fluorine and comprising a basic reagent selected to effectively remove boron contamination from the air stream as said air stream passes through the upstream air filtering bed, said boron contamination resulting from the interaction of fluorine with borosilicate glass in said HEPA filter.

2. The air filtering system of claim 1 wherein said upstream air filtering bed comprises activated carbon particles impregnated with a base.

3. The air filtering system of claim 2 wherein said activated carbon particles are impregnated with KOH.

4. The air filtering system of claim 2 wherein said activated carbon particles are impregnated with KOH at a concentration of 8% by weight or greater.

5. An air filtering system for filtering an air stream for use in a clean room comprising a HEPA (high efficiency particulate air) filter positioned to introduce air into the clean room adjacent to a film deposition system and comprising borosilicate glass, and an upstream air filtering bed positioned upstream of said HEPA filter to receive an air stream from adjacent the film deposition system and comprising a basic reagent selected to effectively remove boron contamination from the air stream as said air stream passes through the upstream air filtering bed, said boron contamination being released from borosilicate glass in said HEPA filter.

6. The air filtering system of claim 5 wherein said upstream air filtering bed comprises activated carbon particles impregnated with a base.

7. An air filtering system for filtering an air stream for use in a clean room comprising a HEPA (high efficiency particulate air) filter positioned to introduce air into the clean room, and an upstream air filtering bed positioned upstream of said HEPA filter to receive from the clean room an air stream containing photoresist compounds and comprising activated carbon impregnated with an antibacterial agent selected to effectively suppress the growth of bacteria on said activated carbon, said bacterial growth resulting from the interaction of photoresist compounds with activated carbon in said upstream air filter.

8. The air filtering system of claim 7 wherein the activated carbon of the upstream air filtering bed is in the form of activated carbon particles in the size range of 20×140 mesh.

9. The air filtering system of claim 7 wherein the antibacterial agent comprises potassium iodide.

10. The air filtering system of claim 7 wherein the antibacterial agent comprises silver.

11. An air filtering system for filtering an air stream for use in a clean room to effectively remove a process-limiting molecular contaminant therefrom comprising sequentially arranged first and second air filtering beds, said first air filtering bed positioned to receive the air stream from the clean room and comprising a first reagent selected to effectively remove the process-limiting molecular contaminant from the air stream as said air stream passes through the first air filtering bed, and said second air filtering bed positioned to receive the air stream that has passed through said first air filtering bed and comprising a second reagent different from said first reagent.

12. The air filtering system of claim 11 wherein said first reagent comprises an acid.

13. The air filtering system of claim 12 wherein said first reagent is citric acid.

14. The air filtering system of claim 12 wherein said first reagent is sulfuric acid.

15. The air filtering system of claim 12 wherein said second reagent comprises a base.

16. The air filtering system of claim 11 wherein said first reagent is $ZnCl_2$.

17. The air filtering system of claim 11 wherein said first reagent is $ZnCl_2$ and said second reagent is KOH.

18. The air filtering system of claim 11 wherein said first filtering bed comprises activated carbon particles impregnated with said first reagent and said second filtering bed comprises activated carbon particles impregnated with said second reagent.

19. The air filtering system of claim 11 further comprising a HEPA (high efficiency particulate air) filter positioned to introduce air into the clean room, wherein said first and second sequentially arranged filtering beds are positioned upstream of said HEPA filter.

* * * * *